(12) United States Patent
Watkins et al.

(10) Patent No.: US 11,129,749 B2
(45) Date of Patent: Sep. 28, 2021

(54) INTEGRATED HELMET CONTROLS

(71) Applicant: A.C.E. International Company, Inc., Taunton, MA (US)

(72) Inventors: James Watkins, East Taunton, MA (US); Ed Martin, Plymouth, MA (US)

(73) Assignee: WALTER SURFACE TECHNOLOGIES INCORPORATED, Windsor, CT (US)

( * ) Notice: Subject to any disclaimer, the term of this patent is extended or adjusted under 35 U.S.C. 154(b) by 795 days.

(21) Appl. No.: 15/871,325

(22) Filed: Jan. 15, 2018

(65) Prior Publication Data

US 2019/0216649 A1 Jul. 18, 2019

(51) Int. Cl.
*A61F 9/06* (2006.01)
(52) U.S. Cl.
CPC .............. *A61F 9/067* (2013.01); *A61F 9/061* (2013.01)
(58) Field of Classification Search
CPC .................................. A61F 9/067; A61F 9/061
See application file for complete search history.

(56) References Cited

U.S. PATENT DOCUMENTS

| | | | | | |
|---|---|---|---|---|---|
| 3,344,434 | A | * | 10/1967 | Beckmann | A61F 9/067 2/8.3 |
| 6,070,264 | A | * | 6/2000 | Hamilton | A61F 9/067 2/8.8 |
| 8,089,424 | B2 | * | 1/2012 | Huh | A61F 9/067 345/8 |
| D683,906 | S | * | 6/2013 | Jackson | D29/110 |
| 8,860,257 | B2 | | 10/2014 | Schiefermuller et al. | |
| D918,483 | S | * | 5/2021 | Bastman | D29/122 |
| 2007/0056073 | A1 | * | 3/2007 | Martin | A61F 9/065 2/8.8 |
| 2008/0060102 | A1 | * | 3/2008 | Matthews | A61F 9/061 2/8.2 |
| 2008/0082179 | A1 | | 4/2008 | Yang | |
| 2009/0094721 | A1 | * | 4/2009 | Becker | G01J 1/02 2/8.8 |

(Continued)

FOREIGN PATENT DOCUMENTS

| | | |
|---|---|---|
| EP | 2 144 045 A1 | 1/2010 |
| EP | 2 193 768 A1 | 6/2010 |

(Continued)

*Primary Examiner* — Alissa J Tompkins
*Assistant Examiner* — Brieanna Szafran
(74) *Attorney, Agent, or Firm* — McClure, Qualey & Rodack, LLP

(57) ABSTRACT

A helmet comprises a shell with an integrated panel tab that is formed by cutting a pattern into the shell. The helmet further comprises an enclosure located interior to the shell and at a position that corresponds to the integrated panel tab. Within the enclosure are an electronic membrane, which is operatively coupled to the integrated panel tab, and a membrane force tab, which is operatively coupled to the electronic membrane. When pressure is applied to the integrated panel tab from the exterior of the shell (by, for example, a finger of a user), the integrated panel tab functions as a flexible actuator that presses the electronic membrane, thereby permitting control of helmet functions without any externally-protruding controls that can be inadvertently broken.

18 Claims, 8 Drawing Sheets

(56) References Cited

U.S. PATENT DOCUMENTS

| | | | |
|---|---|---|---|
| 2010/0132086 A1* | 6/2010 | Huh | A61F 9/067 2/8.2 |
| 2010/0287676 A1* | 11/2010 | Seo | A61F 9/061 2/8.2 |
| 2013/0340141 A1* | 12/2013 | Huh | A61F 9/067 2/8.8 |
| 2015/0320601 A1* | 11/2015 | Gregg | G06T 5/008 345/8 |
| 2016/0022496 A1* | 1/2016 | DeKeuster | G02F 1/13306 349/14 |
| 2017/0042738 A1* | 2/2017 | Yang | A61F 9/067 |
| 2017/0188646 A1* | 7/2017 | Liang | G02B 27/0176 |
| 2017/0258639 A1* | 9/2017 | Wu | G02B 27/0172 |
| 2018/0271709 A1* | 9/2018 | Currie | A61F 9/067 |
| 2019/0143437 A1* | 5/2019 | Hofer Kraner | G02F 1/13318 219/130.01 |

FOREIGN PATENT DOCUMENTS

| | | | | |
|---|---|---|---|---|
| EP | 3192480 A1 * | 7/2017 | | A61F 9/065 |
| WO | 2010/111722 A2 | 10/2010 | | |

* cited by examiner

INTEGRATED HELMET CONTROLS

BACKGROUND

Field of the Disclosure

The present disclosure relates generally to safety equipment and, more particularly, to welding helmets.

Description of Related Art

Conventional welding helmets with auto-darkening features have externally-protruding control mechanisms that allow user adjustment of various settings (e.g., shade, sensitivity, delay, etc.). Unfortunately, these externally-protruding control mechanisms are prone to breaking or changing helmet screen settings unintentionally when the user inadvertently contacts the externally-protruding control mechanism.

SUMMARY

The present disclosure provides a helmet. The helmet comprises a shell with an integrated panel tab that is formed by cutting a pattern into the shell. The helmet further comprises an enclosure located interior to the shell and at a position that corresponds to the integrated panel tab. Within the enclosure are an electronic membrane, which is operatively coupled to the integrated panel tab, and a membrane force tab, which is operatively coupled to the electronic membrane. When pressure is applied to the integrated panel tab from the exterior of the shell (by, for example, a finger of a user), the integrated panel tab functions as a flexible actuator that presses the electronic membrane, thereby permitting control of helmet functions without any externally-protruding controls that can be inadvertently broken.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

Figure 1:
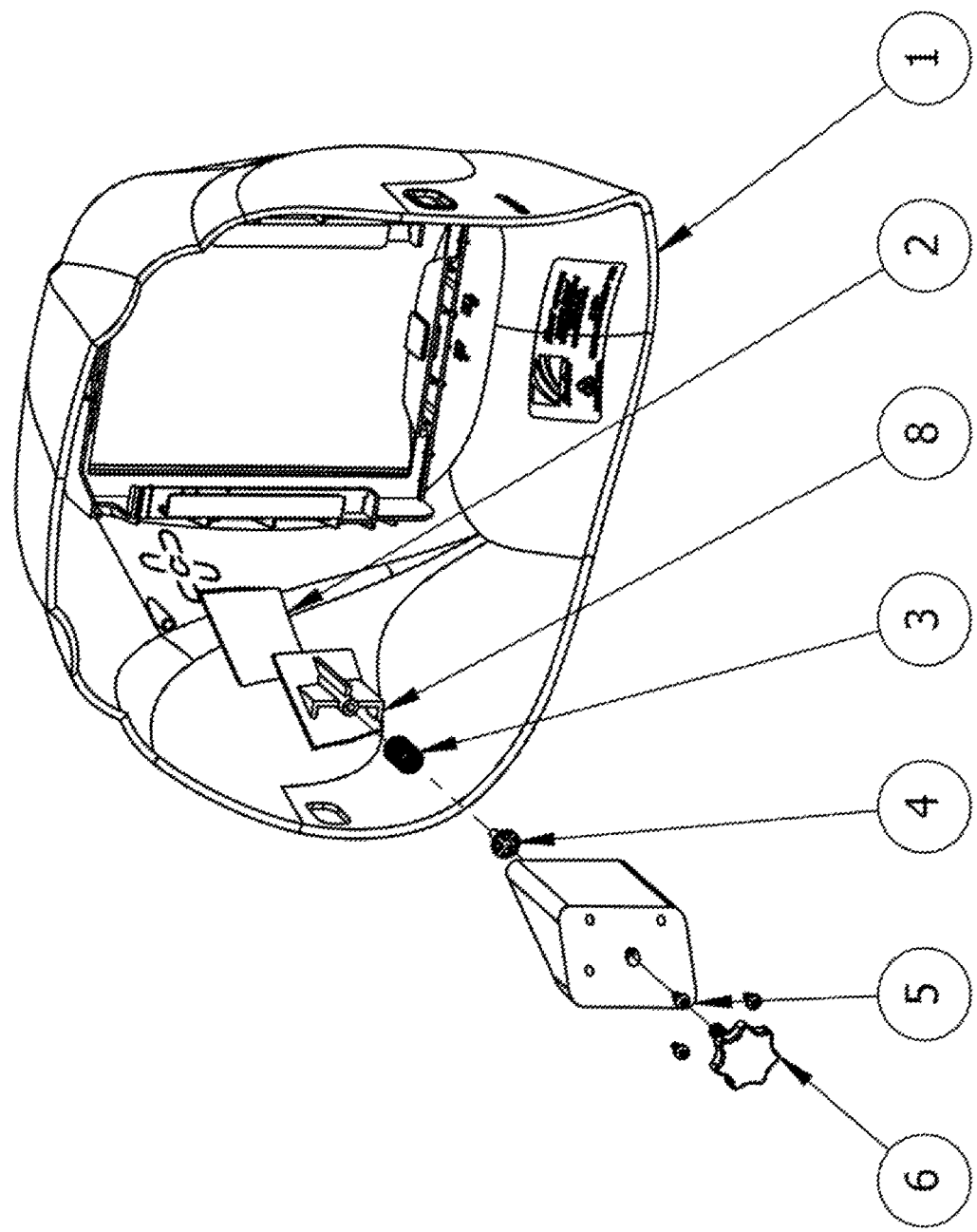
FIG. 1 is a drawing of one embodiment of a helmet shell, which shows a perspective view of an interior the shell.

Welding helmets with auto-darkening features require controls. Conventionally, those controls exist as externally-protruding buttons that allow users to adjust various settings (e.g., shade, sensitivity, delay, etc.). Unfortunately, these externally-protruding buttons are prone to breaking. Furthermore, because the externally-protruding buttons have a greater likelihood of becoming caught on something, there is also a corresponding increase in the likelihood that helmet filter settings are unintentionally changed by inadvertent contact from the user.

To remedy this drawback, the present disclosure provides a helmet shell with an integrated panel tab that is formed by cutting a pattern into the shell. The integrated panel tab functions as a flexible actuator, thereby removing the need for externally-protruding helmet controls. An enclosure is located interior to the shell and at a position that corresponds to the integrated panel tab. Within the enclosure is an electronic membrane, which is operatively coupled to the integrated panel tab. Thus, when pressure is applied to the integrated panel tab from the exterior of the shell (by, for example, a finger of a user), the applied pressure causes the integrated panel tab to flex and relay at least a portion of the applied pressure to the electronic membrane. A membrane force plate, also located in the enclosure, provides a countervailing force to pressure on the integrated panel tab, thereby keeping the electronic membrane in place.

Because the integrated panel tab functions as a flexible actuator that relays at least a portion of that force to the electronic membrane, the disclosed helmet has no externally-protruding controls that can be inadvertently broken. Furthermore, because no externally-protruding buttons exist on the disclosed shell, the chances are reduced for a user to inadvertently change helmet filter settings (or helmet adjustable screen settings).

Having provided a broad description of one embodiment of an inventive helmet shell with integrated controls, along with its corresponding advantages, reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

Figure 2:
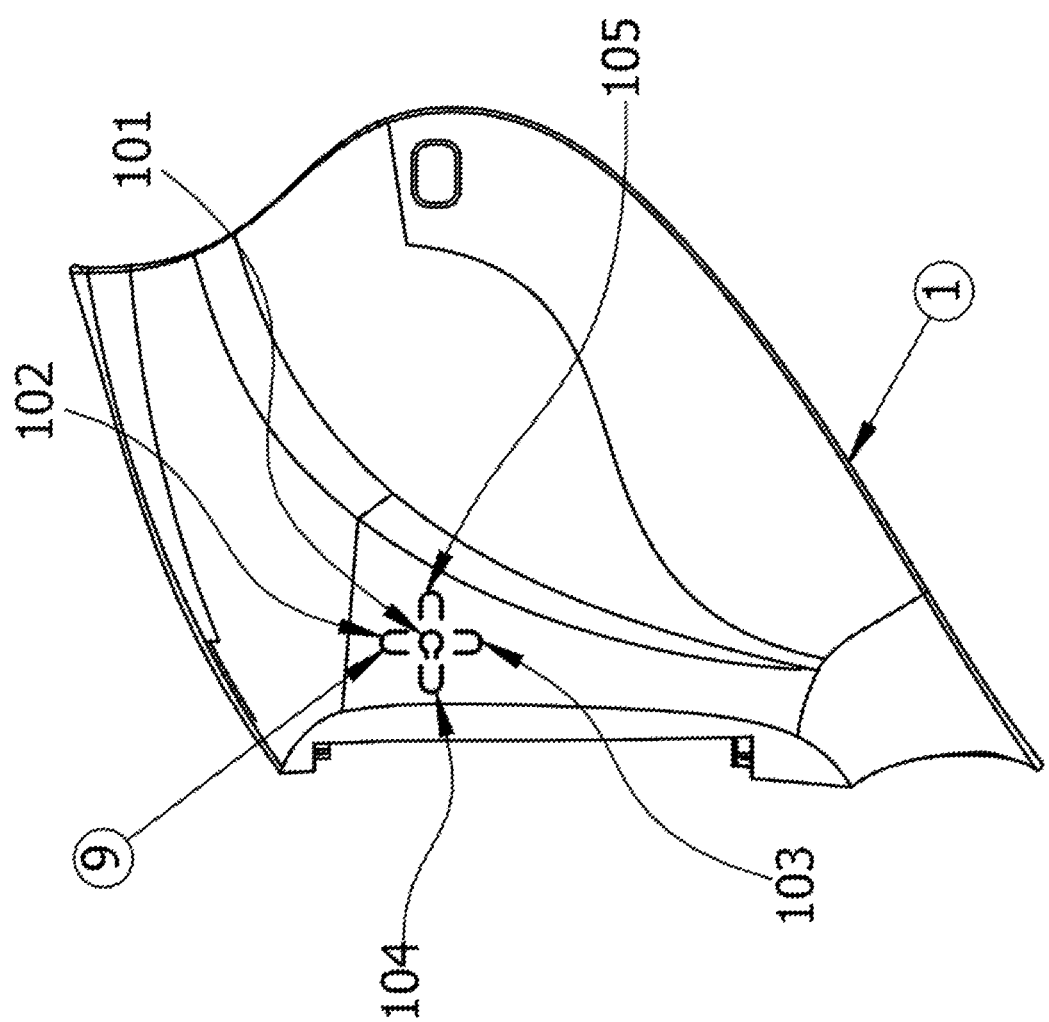
FIG. 2 is a drawing showing a left profile view of the shell of FIG. 1.
Figure 3:
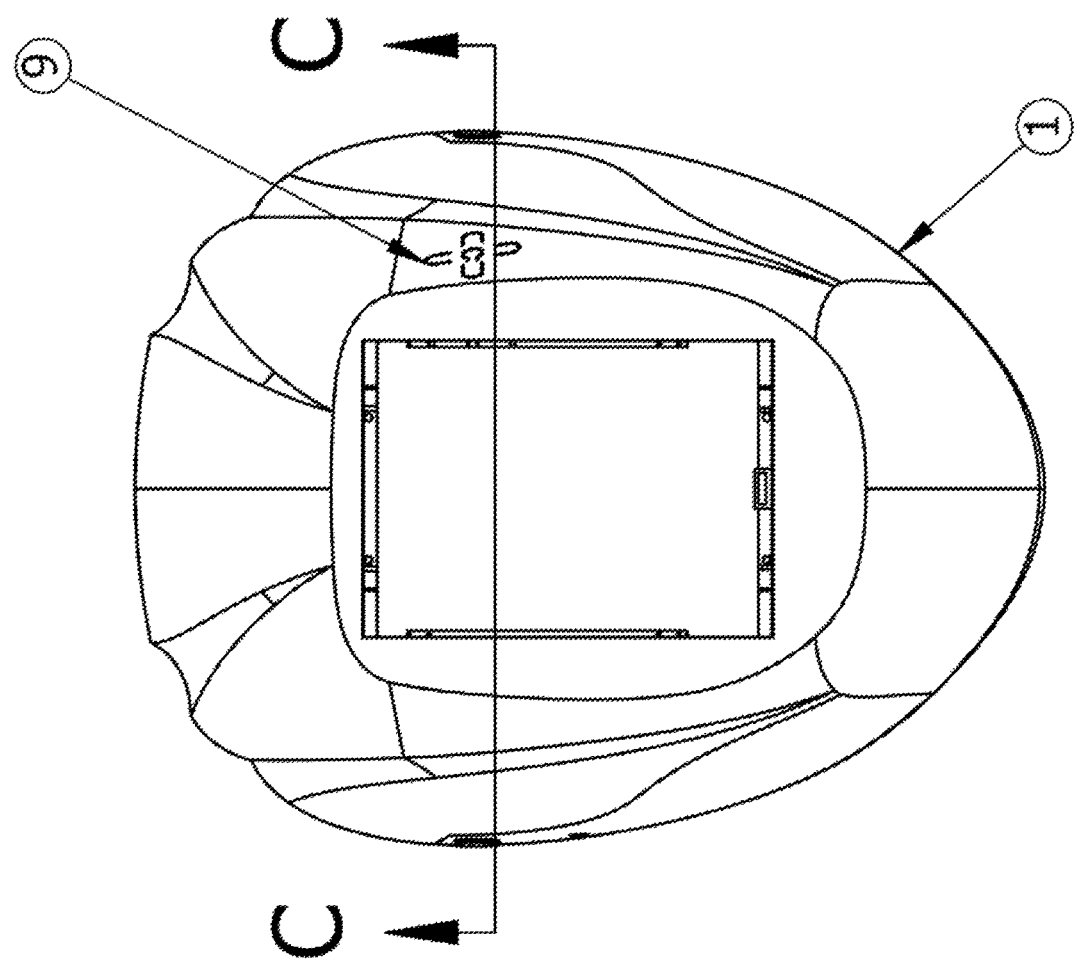
FIG. 3 is a drawing showing a front profile view from an exterior of the shell of FIG. 1.
Figure 4:
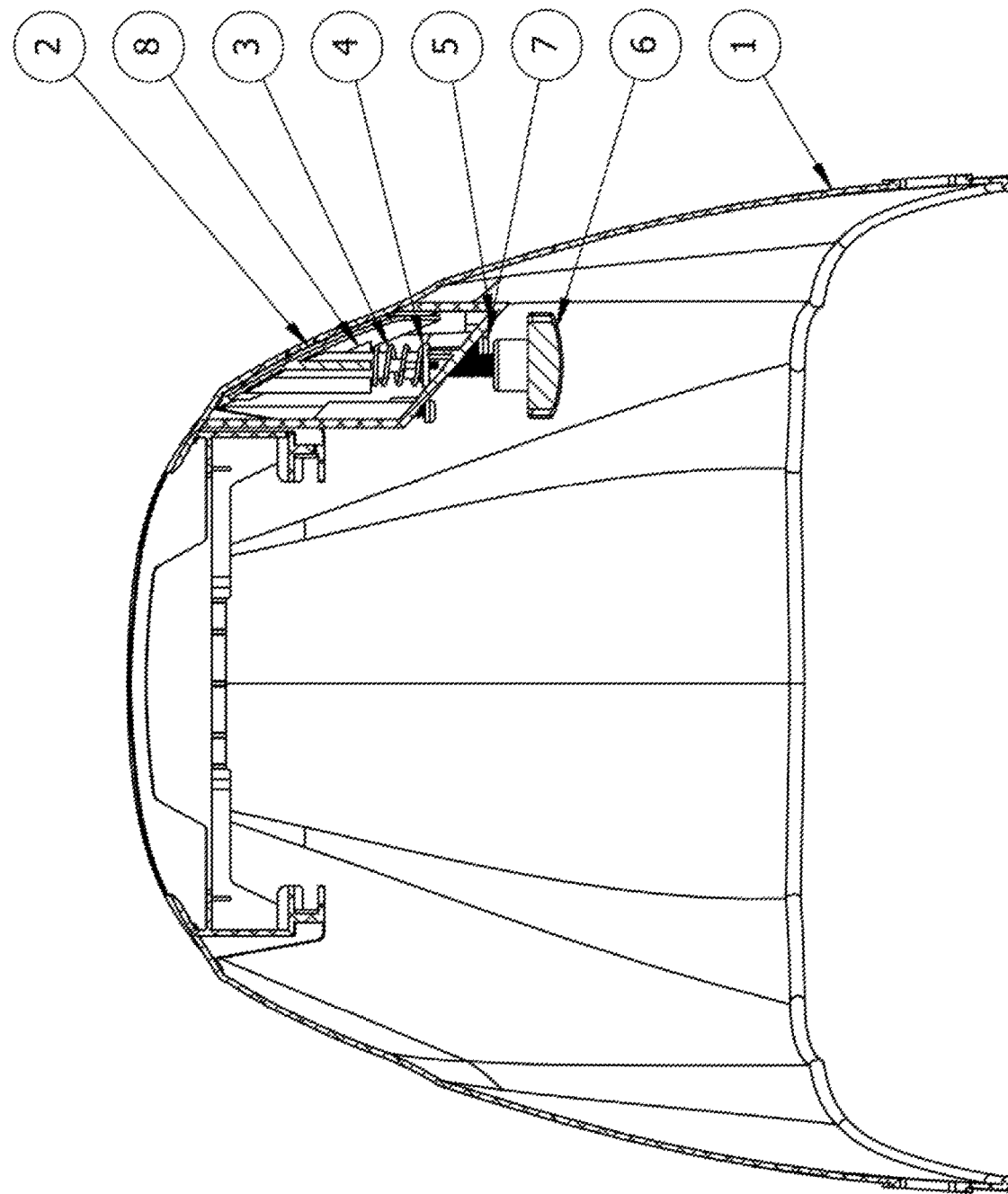
FIG. 4 is a drawing showing a sectional view of the shell, cut along section C-C, as labeled in FIG. 3.

FIG. 1 shows a perspective view of an interior a welding helmet shell, while FIGS. 2, 3, and 4 show a left profile view, a front profile view (as seen from an exterior of the shell), and a sectional view, respectively. As shown in FIGS. 1 through 4, the helmet comprises a helmet shell 1 (or simply called a shell), an electronic printed circuit board (PCB) comprising either a relatively-hard or a relatively-soft membrane-like material 2 (or simply designated herein as electronic membrane 2), a compression spring 3, a force transfer pin 4, an enclosure 5, an adjustment knob 6, one or more screws 7, a membrane force plate 8, and a slot pattern 9 that is cut into the shell 1. As shown in FIG. 2, the slot pattern 9 forms integrated panel tabs 101, 102, 103, 104, 105. By way of example, the integrated panel tabs 101, 102, 103, 104, 105 are formed by cutting U-shaped slots in the shell 1 itself, thereby avoiding externally-protruding controls.

Figure 5:
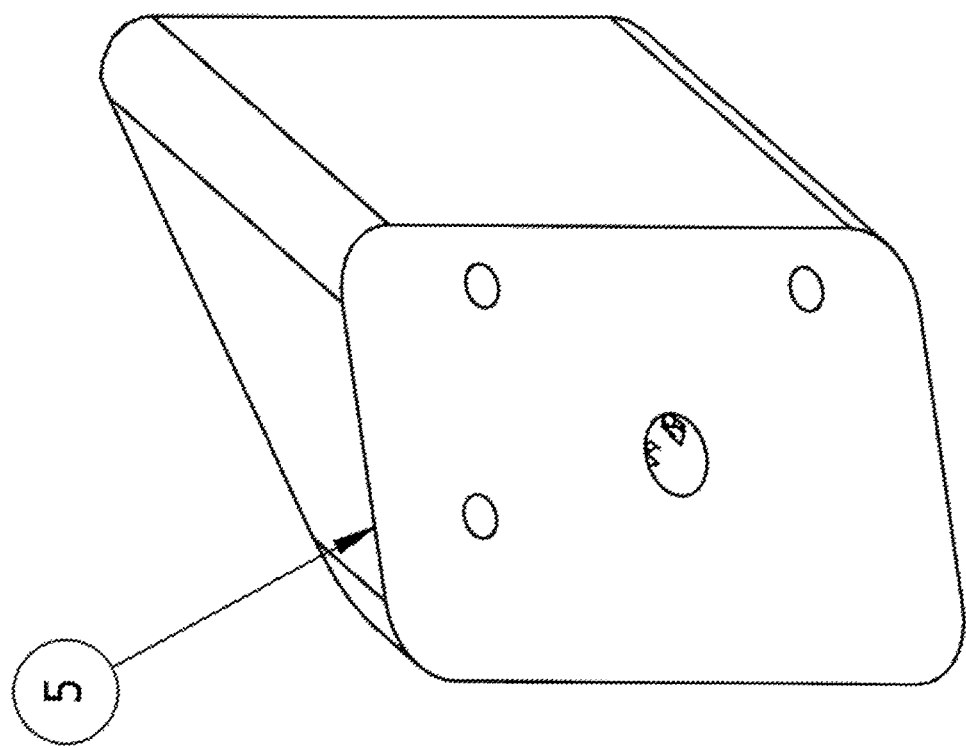
FIG. 5 is a drawing showing one embodiment of an enclosure.

When assembled, the helmet comprises the shell 1 with the integrated panel tabs 101, 102, 103, 104, 105 formed by cutting slot patterns 9 into the shell 1. The enclosure 5 is located in an interior of the shell 1 at a position that corresponds to where the slot pattern 9 is formed. As one will appreciate, the side of the shell 1 that faces toward a user is referred to herein as the interior of the shell 1, while the side of the shell 1 that faces away from the user is referred to herein as the exterior of the shell 1. One embodiment of the enclosure 5 is shown in greater detail in FIG. 5, and as shown in FIG. 5 the enclosure 5 comprises a threaded hole.

Figure 8:
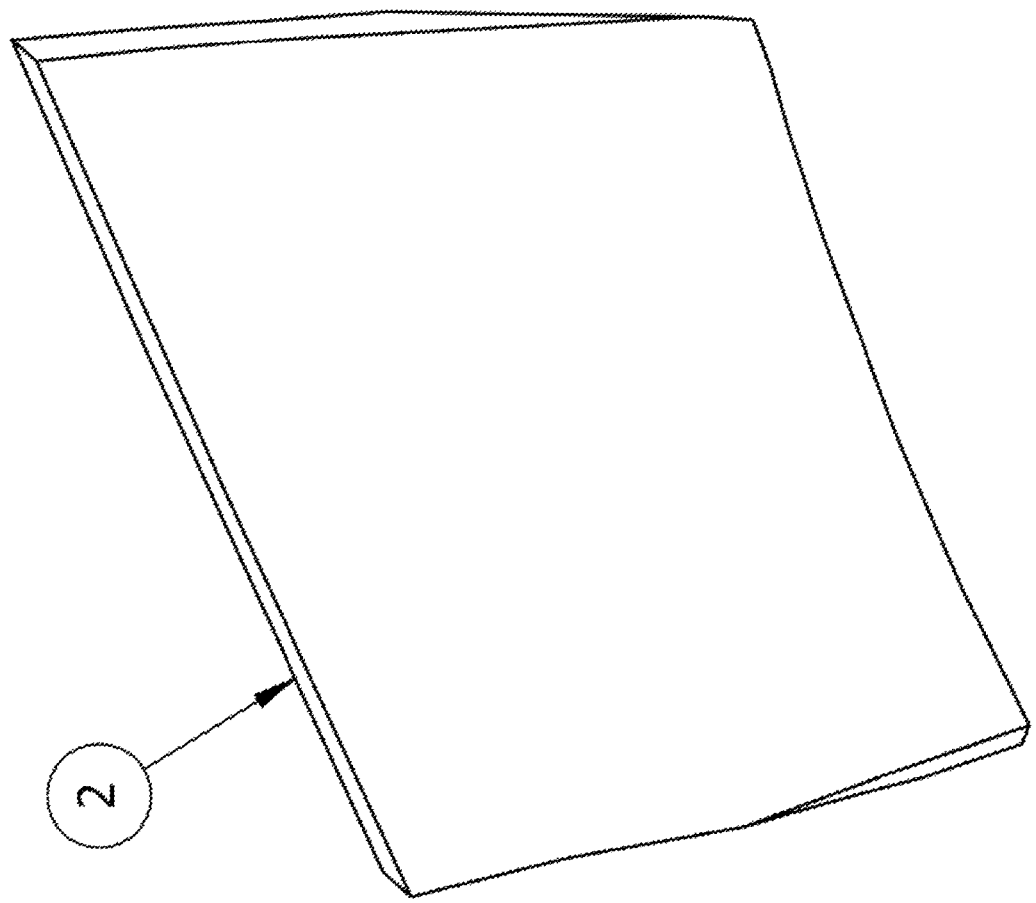
FIG. 8 is a drawing showing one embodiment of an electronic printed circuit board (PCB) comprising either a relatively-hard or relatively-soft membrane-like material.

The electronic membrane 2 is positioned within the enclosure 5. One embodiment of the electronic membrane 2 is shown in greater detail in FIG. 8. Because the structure, form, and function of such electronic membranes 2 are known in the art, only a truncated discussion of electronic membranes 2 is provided. When one of the integrated panel tabs 101, 102, 103, 104, 105 is pressed by the user, the applied pressure is conveyed to the electronic membrane 2, which is connected to the programmable controlling mechanism (not shown). For some embodiments, a printed circuit board (PCB) with micro-switches are substitutable for the integrated panel tabs 101, 102, 103, 104, 105. It should also be appreciated that each of the integrated panel tabs 101, 102, 103, 104, 105 deflects or flexes substantially independently of any of the other integrated panel tabs 101, 102, 103, 104, 105.

Figure 6:
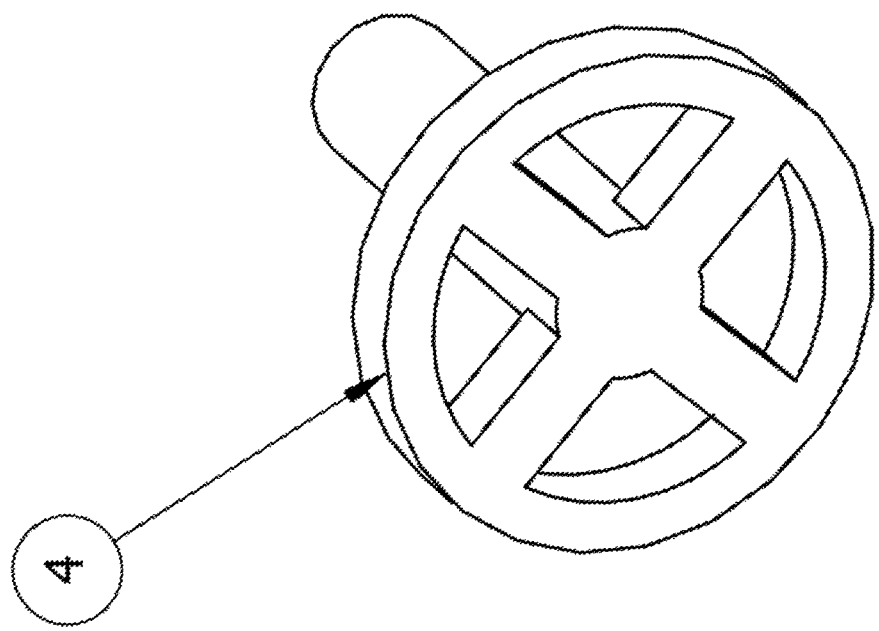
FIG. 6 is a drawing showing one embodiment of a force transfer pin.
Figure 7:
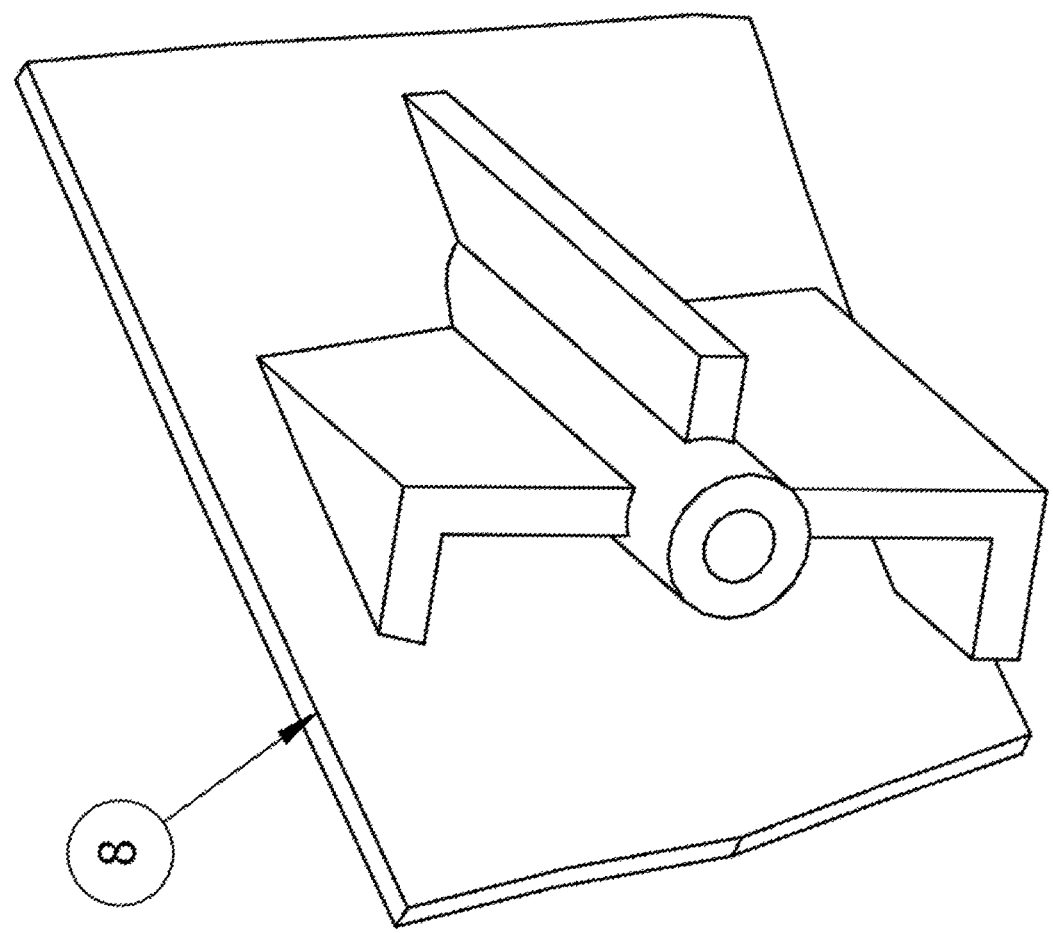
FIG. 7 is a drawing showing one embodiment of a membrane force plate.

The electronic membrane 2 is operatively coupled to a membrane force plate 8, which is also located in the enclosure 5. One embodiment of the membrane force plate 8 is shown in greater detail in FIG. 7. The membrane force plate 8 serves to keep in place the electronic membrane 2. In the embodiment of FIGS. 1 through 4, the helmet further comprises a compression spring 3, which is also located within the enclosure 5. The compression spring 3 is operatively coupled to the membrane force plate 8 and applies a force to the membrane force plate 8. The helmet of FIGS. 1 through 4 further comprises a force transfer pin 4, which is also located within the enclosure 5. One embodiment of the force transfer pin 4 is shown in greater detail in FIG. 6. As shown in greater detail through FIGS. 6 and 7, the force transfer pin 4 comprises a head and a shank, while the membrane force plate 8 comprises a plate hole. When assembled, the shank of the force transfer pin 4 aligns with the plate hole. The compression spring 3 surrounds the shank of the force transfer pin 4 and is positioned between the head of the force transfer pin 4 and the membrane force plate 8. In this configuration, the head and the membrane force plate 8 work cooperatively to maintain the compression spring 3 around the shank and, further, to apply a compression force to the spring 3.

The embodiment of FIGS. 1 through 4 further comprises an adjustment knob 6 with a threaded shank. The threaded shank inserts into the threaded hole of the enclosure 5, with one end of the shank operatively coupling to the head of the force transfer pin 4. Thus, the compression force on the compression spring 3 becomes adjustable by turning the adjustment knob 6. With the electronic membrane 2, the membrane force plate 8, the compression spring 3, and the force transfer pin 4 properly placed within the enclosure 5, the enclosure is secured to the shell 1 by one or more screws 7, as shown in the cutaway view of FIG. 4.

Turning now to the slot pattern 9, in the embodiment of FIGS. 1 through 4, the slot pattern 9 includes a central tab 101, an upper tab 102, a lower tab 103, a front tab 104, and a rear tab 105. Functionally, in this embodiment, the central tab 101 toggles through a selection of modes, such as shade, sensitivity, delay, work time, or other functions that can be programmed into an adjustable-darkness helmet. The upper tab 102 increases a value for the selected mode, while the lower tab 103 decreases the value for the selected mode. For some embodiments, the front tab 104 selects a next mode, while the rear tab 105 selects a previous mode. Although specific functions are described to better understand the functioning of the integrated panel tabs 101, 102, 103, 104, 105, it should be appreciated that the integrated panel tabs 101, 102, 103, 104, 105 can be programmed for different functions, as desired or needed. At bottom, these integrated panel tabs 101, 102, 103, 104, 105 serve as means for controlling helmet screen settings by applying a force directly to a portion of the shell 1. Although not shown in FIGS. 1 through 4, those having skill in the art will understand that an adjustable screen (with controllable settings) mounts to the inside of the shell 1.

As shown in FIGS. 1 through 8, because the integrated panel tabs 101, 102, 103, 104, 105 function as flexible actuators that relay at least a portion of an applied force to the electronic membrane 2, the disclosed helmet has no externally-protruding controls that can be inadvertently broken. Furthermore, because no externally-protruding buttons exist on the disclosed shell 1, the chances are reduced for a user to inadvertently change helmet screen settings.

Figure 9:
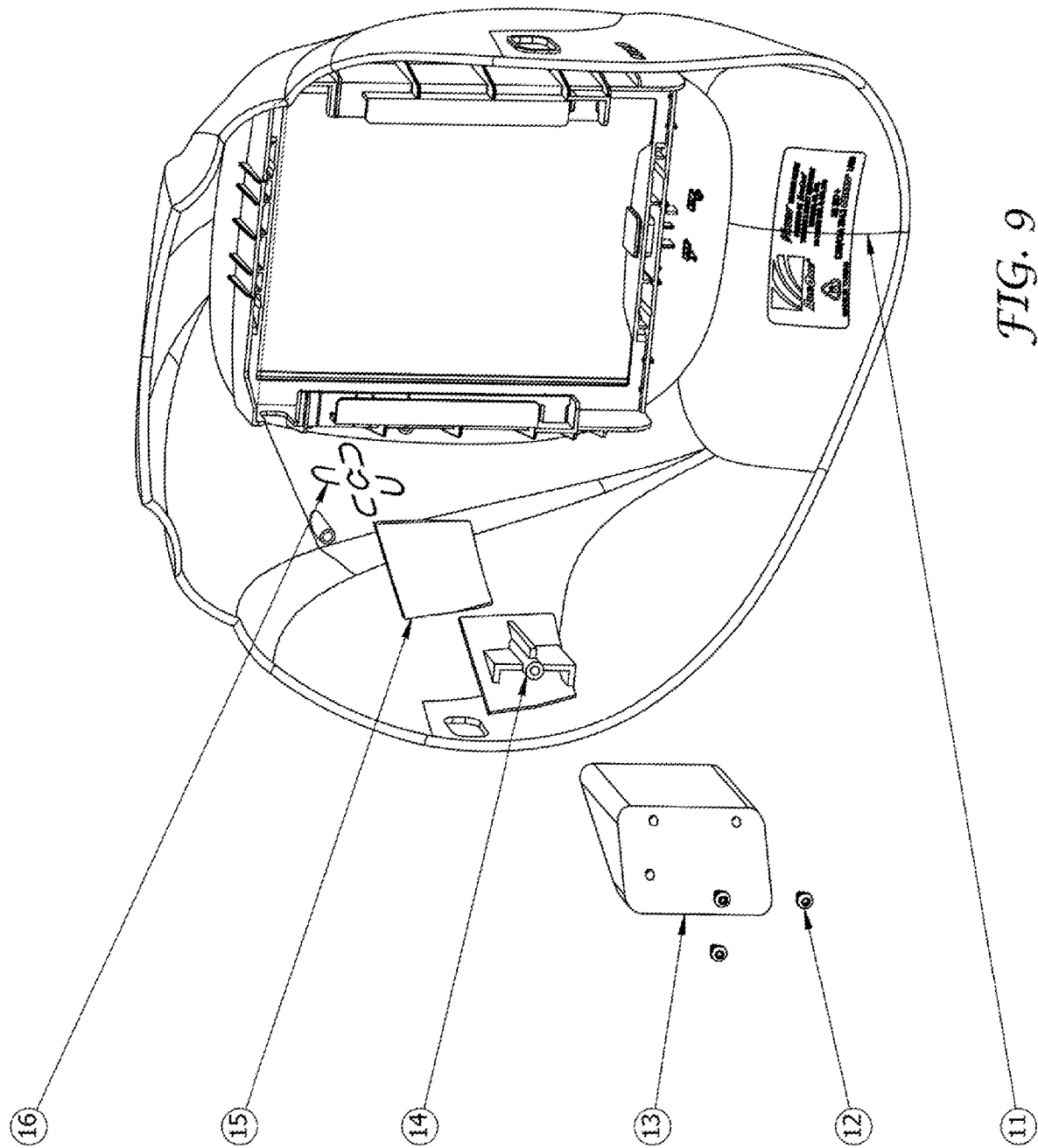
FIG. 9 is a drawing of another embodiment of a helmet shell, which applies a fixed force.

Unlike the embodiment of FIGS. 1 through 4 (which shows a variable or adjustable force applied to the electronic membrane 2), FIG. 9 shows one embodiment of a helmet that has a fixed force applied to an electronic membrane 14. Similar to FIGS. 1 through 4, the embodiment of FIG. 9 comprises a shell 11 with a slot pattern 16 that is cut into the shell 11 itself. However, unlike FIGS. 1 through 4, the embodiment of FIG. 9 comprises an enclosure 13 that does not have a threaded hole. Also, unlike FIGS. 1 through 4, the embodiment of FIG. 9 does not require a force transfer pin. Instead, the membrane force plate 14 applies a fixed force to the electronic membrane 15. The electronic membrane 15 and the membrane force plate 14 are kept in place by the enclosure 13, which is secured to the shell 11 by screws 12.

Again, because the disclosed helmet has no externally-protruding controls or externally-protruding buttons, there is less likelihood that a user will inadvertently change helmet screen settings or physically break the controls.

Although exemplary embodiments have been shown and described, it will be clear to those of ordinary skill in the art that a number of changes, modifications, or alterations to the disclosure as described may be made. All such changes, modifications, and alterations should therefore be seen as within the scope of the disclosure.

What is claimed is:
1. A helmet, comprising:
a shell;
integrated panel tabs formed by cutting a pattern into the shell, the integrated panel tabs comprising:
a central tab formed by cutting a first slot in the shell;
an upper tab formed by cutting a second slot in the shell;
a lower tab formed by cutting a third slot in the shell;
a front tab formed by cutting a fourth slot in the shell;
a rear tab formed by cutting a fifth slot in the shell;
an enclosure located in an interior of the shell at a position corresponding to the integrated panel tabs, the enclosure comprising a threaded hole;

an electronic membrane positioned within the enclosure, the electronic membrane being operatively coupled to the integrated panel tabs;
a membrane force plate located within the enclosure, the membrane force plate comprising a plate hole;
a force transfer pin located within the enclosure, the force transfer pin having a head and a shank; the shank being aligned with the plate hole;
a compression spring located within the enclosure, the compression spring being positioned between the head and the membrane force plate; the compression spring surrounding the shank, the head and the membrane force plate cooperatively maintaining the compression spring around the shank, the head and the membrane force plate cooperatively applying a compression force to the compression spring; and
an adjustment knob comprising a threaded shank; the threaded shank being inserted into the threaded hole, the threaded shank being operatively coupled to the head, the compression force being adjustable by turning the adjustment knob.

2. The helmet of claim 1, further comprising:
screws securing the enclosure to the shell.

3. The helmet of claim 1, further comprising:
an adjustable screen secured to the shell, the adjustable screen having at least one controllable settings, said at least one controllable setting being controlled by at least one of the integrated panel tabs.

4. The helmet of claim 3, wherein:
the adjustable screen has a plurality of modes,
the at least one controllable setting comprising at least one of selecting one of said plurality of modes and adjusting a value of one of said plurality of modes.

5. The helmet of claim 1, wherein each of the integrated panel tabs deflects and flexes independently of any of the other integrated panel tabs.

6. A helmet, comprising:
a shell;
at least one integrated panel tab formed by cutting a pattern into the shell;
an enclosure located in an interior of the shell at a position corresponding to the at least one integrated panel tab;
an electronic membrane positioned within the enclosure, the electronic membrane being operatively coupled to the at least one integrated panel tab;
a membrane force plate located within the enclosure, the membrane force plate being operatively coupled to the electronic membrane; and
a compression spring located within the enclosure and operatively coupled to the membrane force plate, the compression spring applying a force to the membrane force plate.

7. The helmet of claim 6, wherein said at least one integrated panel tab comprises:
a central tab formed by cutting a first slot into the shell;
an upper tab formed by cutting a second slot into the shell;
a lower tab formed by cutting a third slot into the shell;
a front tab formed by cutting a fourth slot into the shell; and
a rear tab formed by cutting a fifth slot into the shell.

8. The helmet of claim 7, further comprising:
an adjustable screen secured to the shell, the adjustable screen having controllable settings, said controllable settings being controlled by at least one of said central, upper, lower, front and rear tabs.

9. The helmet of claim 7, wherein each of said at least one integrated panel tabs deflects and flexes independently of any of the other said at least one integrated panel tabs.

10. The helmet of claim 6, further comprising:
a plate hole located on the membrane force plate;
a force transfer pin located within the enclosure, the force transfer pin having a head and a shank, the shank being aligned with the plate hole, the compression spring being positioned between the head and the membrane force plate, the compression spring surrounding the shank, the head and the membrane force plate cooperatively maintaining the compression spring around the shank, the head and the membrane force plate cooperatively applying a compression force to the compression spring.

11. The helmet of claim 10, further comprising:
a threaded hole located on the enclosure;
an adjustment knob having a threaded shank, the threaded shank being inserted into the threaded hole, the threaded shank being operatively coupled to the head of the force transfer pin, the compression force being adjustable by turning the adjustment knob.

12. The helmet of claim 6, further comprising:
screws securing the enclosure to the shell.

13. The helmet of claim 6, further comprising:
an adjustable screen secured to the shell, the adjustable screen having a controllable setting, the controllable setting being controlled by said at least one integrated panel tab.

14. A helmet, comprising:
a shell;
at least one integrated panel tab formed by cutting a pattern into the shell;
an enclosure located in an interior of the shell at a position corresponding to said at least one integrated panel tab;
an electronic membrane positioned within the enclosure, the electronic membrane being operatively coupled to said at least one integrated panel tab;
a membrane force plate located within the enclosure, the membrane force plate being operatively coupled to the electronic membrane;
a compression spring located within the enclosure and operatively coupled to the membrane force plate, the compression spring applying a force to the member force plate; and an adjustable screen secured to the shell, the adjustable screen having a controllable setting, the controllable setting being controlled by said at least one integrated panel tab.

15. The helmet of claim 14, further comprising:
a plate hole located on the membrane force plate;
a force transfer pin located within the enclosure, the force transfer pin having a head and a shank, the shank being aligned with the plate hole, the compression spring being positioned between the head and the membrane force plate, the compression spring surrounding the shank, the head and the membrane force plate cooperatively maintaining the compression spring around the shank, the head and the membrane force plate cooperatively applying a compression force to the compression spring.

16. The helmet of claim 15, further comprising:
a threaded hole located on the enclosure;
an adjustment knob having a threaded shank, the threaded shank being inserted into the threaded hole, the threaded shank being operatively coupled to the head of the force transfer pin, the compression force being adjustable by turning the adjustment knob.

17. The helmet of claim 14, wherein said at least one integrated panel tab comprises:
- a central tab formed by cutting a first slot into the shell;
- an upper tab formed by cutting a second slot into the shell;
- a lower tab formed by cutting a third slot into the shell;
- a front tab formed by cutting a fourth slot into the shell; and
- a rear tab formed by cutting a fifth slot into the shell.

18. The helmet of claim 17, wherein each of said at least one integrated panel tabs deflects and flexes independently of any of the other said at least one integrated panel tabs.

\* \* \* \* \*